(12) United States Patent
Kishimoto et al.

(10) Patent No.: US 9,527,802 B2
(45) Date of Patent: Dec. 27, 2016

(54) METHOD OF MANUFACTURING COUMARAMIDE

(71) Applicant: Toray Industries, Inc., Tokyo (JP)

(72) Inventors: Jumpei Kishimoto, Kanagawa (JP);
Atsushi Minamino, Kanagawa (JP);
Hiroyuki Kurihara, Kanagawa (JP);
Katsushige Yamada, Kanagawa (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/419,550

(22) PCT Filed: Aug. 8, 2013

(86) PCT No.: PCT/JP2013/071544
§ 371 (c)(1),
(2) Date: Feb. 4, 2015

(87) PCT Pub. No.: WO2014/024989
PCT Pub. Date: Feb. 13, 2014

(65) Prior Publication Data
US 2015/0218087 A1    Aug. 6, 2015

(30) Foreign Application Priority Data

Aug. 10, 2012  (JP) ................................. 2012-178550

(51) Int. Cl.
*C07C 231/24*   (2006.01)
*C07C 235/34*   (2006.01)

(52) U.S. Cl.
CPC .................................. *C07C 231/24* (2013.01)

(58) Field of Classification Search
CPC ............................ C07C 231/24; C07C 235/34
(Continued)

(56) References Cited

U.S. PATENT DOCUMENTS

2011/0250637 A1\* 10/2011 Kurihara .............. B01D 61/022
435/41
2013/0004994 A1  1/2013 Hanakawa et al.
(Continued)

FOREIGN PATENT DOCUMENTS

CA           2 864 256 A1    8/2013
JP          2008-161125 A    7/2008
(Continued)

OTHER PUBLICATIONS

Cevasco ("Participation of an Extended p-Oxo Ketene Intermediate in the Dissociative Alkaline Hydrolysis of Aryl 4-Hydroxycinnamates" J. Org. Chem. 1994, 59, 6274).\*
(Continued)

*Primary Examiner* — Jafar Parsa
*Assistant Examiner* — Amy C Bonaparte
(74) *Attorney, Agent, or Firm* — DLA Piper LLP (US)

(57) ABSTRACT

A method of manufacturing coumaramide includes treating cellulose-based biomass with an ammonia-containing treatment agent to obtain ammonia-treated biomass, immersing the ammonia-treated biomass into a solvent containing at least water and eluting coumaramide in the ammonia-treated biomass into the solvent to obtain a coumaramide solution, and precipitating coumaramide in the coumaramide solution as a crystal to obtain a coumaramide crystal.

9 Claims, 6 Drawing Sheets

(58) Field of Classification Search
USPC .......................................... 435/267; 564/170
See application file for complete search history.

(56) References Cited

U.S. PATENT DOCUMENTS

| | | |
|---|---|---|
| 2013/0092157 A1 | 4/2013 | Hanakawa et al. |
| 2014/0178937 A1 | 6/2014 | Minamino et al. |
| 2014/0287461 A1 | 9/2014 | Kurihara et al. |
| 2015/0004647 A1* | 1/2015 | Niwa .................. C13K 1/02 435/72 |

FOREIGN PATENT DOCUMENTS

| | | |
|---|---|---|
| WO | 2010/067785 A1 | 6/2010 |
| WO | WO 2010/067785 * | 6/2010 |
| WO | WO 2011/103189 * | 8/2011 |
| WO | 2011/111451 A1 | 9/2011 |
| WO | 2011/162009 A1 | 12/2011 |
| WO | 2013/018694 A1 | 2/2013 |
| WO | 2013/122051 A1 | 8/2013 |

OTHER PUBLICATIONS

Michael J. Bowman et al., "Liquid chromatography-mass spectrometry investigation of enzyme-resistant xylooligosaccharide structures of switchgrass associated with ammonia pretreatment, enzymatic saccharification, and fermentation," Bioresource Technology, Jan. 28, 2012, vol. 110, pp. 437-447.

* cited by examiner

METHOD OF MANUFACTURING COUMARAMIDE

TECHNICAL FIELD

This disclosure relates to a method of manufacturing coumaramide that manufactures coumaramide from cellulose-based biomass.

BACKGROUND

Fermentative production processes for chemicals with sugars as raw materials are used for the production of various industrial raw materials. Currently, as sugars to be fermentation raw materials, for example, sugars originated from food raw materials such as sugarcane, starch, and sugar beets are industrially used. However, there is concern that food raw materials will run short, and their prices will soar in the future due to an increase in world population, posing a problem of the construction of a process that efficiently manufactures sugar solutions from reproducible non-food resources, that is, cellulose-based biomass.

The cellulose-based biomass mainly contains lignin as an aromatic polymer and cellulose and hemicellulose as polymers of monosaccharides. Examples of a method of manufacturing a sugar solution with the cellulose-based biomass as a raw material include a method that directly hydrolyzes the cellulose-based biomass as the raw material using concentrated sulfuric acid or the like and a pretreatment-enzymatic saccharification method that performs pretreatment such as digesting treatment, pulverizing treatment, and dilute sulfuric treatment on the cellulose-based biomass in advance to desorb the cellulose and hemicellulose from the lignin and then performs hydrolysis with a diastatic enzyme such as cellulase.

The pretreatment-enzymatic saccharification method in general has an advantage of having a lower environmental load than the method that directly hydrolyzes raw materials, while having a low yield of sugars. In view of this, a method of pretreatment using an ammonia-containing treating agent is developed as a pretreatment method that has a lower environmental load and can obtain a high sugar yield (refer to Japanese Laid-open Patent Publication No. 2008-161125, for example).

However, while it is known that the method of pretreatment using the ammonia-containing treating agent improves the enzymatic saccharification efficiency of the cellulose-based biomass, no sufficient consideration has been given to chemical reactions that occur in the cellulose-based biomass by the method of pretreatment using the ammonia-containing treating agent and resultant specific compounds.

In view of the above circumstances, it could be helpful to identify a substance originated from the cellulose-based biomass obtained by treating with the ammonia-containing treating agent and establish a method of collecting the substance.

SUMMARY

We found that the ammonia-treated biomass pretreated with the ammonia-containing treating agent contains coumaramide as the compound originated from the cellulose-based biomass and discovered a method of extracting high-purity coumaramide from the ammonia-treated biomass.

We thus provide:
(1) A method of manufacturing coumaramide, the method including:

a pretreatment step of treating cellulose-based biomass with an ammonia-containing treating agent to obtain ammonia-treated biomass;

an extraction step of immersing the ammonia-treated biomass into a solvent containing at least water and eluting coumaramide in the ammonia-treated biomass into the solvent to obtain a coumaramide solution; and a crystallization step of precipitating coumaramide in the coumaramide solution as a crystal to obtain a coumaramide crystal.

(2) The method of manufacturing coumaramide according to (1), wherein the coumaramide crystal collected at the crystallization step has a purity of 90% or higher.

(3) The method of manufacturing coumaramide according to (1) or (2), wherein the temperature of the solvent used at the extraction step is 40° C. or higher.

(4) The method of manufacturing coumaramide according to any one of (1) to (3), wherein the solvent used at the extraction step contains at least one polar organic solvent.

(5) The method of manufacturing coumaramide according to (4), wherein the solvent contains at least ethanol as the polar organic solvent.

(6) The method of manufacturing coumaramide according to any one of (1) to (5), wherein the crystallization step includes, before precipitating the crystal from the coumaramide solution, a concentrating step of filtrating the coumaramide solution through a reverse osmosis membrane and collecting a coumaramide concentrate as a non-permeate.

(7) The method of manufacturing coumaramide according to (6), wherein the liquid temperature of the coumaramide solution filtrated through the reverse osmosis membrane is 20° C. or higher.

(8) The method of manufacturing coumaramide according to any one of (1) to (7), wherein the crystallization step precipitates the coumaramide crystal by cooling the coumaramide solution to 15° C. or lower.

(9) The method of manufacturing coumaramide according to any one of (1) to (8), wherein the extraction step hydrolyzes the ammonia-treated biomass through addition of a diastatic enzyme when the ammonia-treated biomass is immersed into the solvent.

(10) The method of manufacturing coumaramide according to any one of (1) to (9), wherein the crystallization step includes, before obtaining the crystal from the coumaramide solution, a purifying step of filtrating the coumaramide solution through a nanofiltration membrane and collecting a purified coumaramide solution as a permeate.

It is thus possible to obtain high-purity coumaramide from ammonia-treated biomass obtained by treating cellulose-based biomass with an ammonia-containing treating agent.

DETAILED DESCRIPTION

The following describes our methods in detail with reference to the drawings. The following examples for carrying out the methods do not limit the scope of this disclosure.

Figure 1:
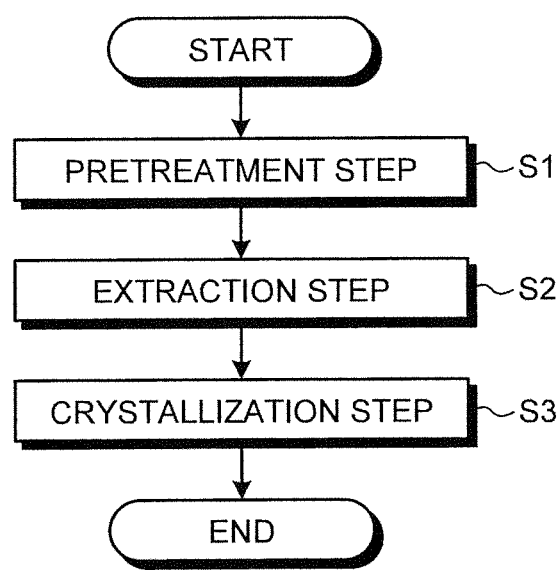
FIG. 1 is a flowchart illustrating an example of our method of manufacturing coumaramide.

The method of manufacturing coumaramide will be described with reference to the accompanying drawings. FIG. 1 is a flowchart illustrating an example of the method of manufacturing coumaramide. As illustrated in FIG. 1, the method of manufacturing coumaramide includes the following steps:

(1) a pretreatment step of treating cellulose-based biomass with an ammonia-containing treatment agent to obtain ammonia-treated biomass (Step S1);

(2) an extraction step of immersing the ammonia-treated biomass into a solvent containing at least water and eluting coumaramide in the ammonia-treated biomass into the solvent to obtain a coumaramide solution (Step S2); and (3) a crystallization step of precipitating coumaramide in the coumaramide solution as a crystal to obtain a coumaramide crystal (Step S3)

The following describes an example to carry out the method in order of steps.

(1) Pretreatment Step

At the pretreatment step, first, the cellulose-based biomass is treated with the ammonia-containing treating agent to obtain the ammonia-treated biomass. Examples of the cellulose-based biomass herein include herbaceous biomass such as bagasse, switchgrass, napier grass, erianthus, corn stover (stems and leaves of corn), corncobs (cores of corn), beet pulp, cottonseed hulls, empty fruit bunches, rice straw, wheat straw, bamboo, and bamboo grass; trees such as silver birches, beeches, and poplars; and waste construction materials.

In general, examples of a method of pretreating cellulose-containing biomass include digesting treatment, pulverizing treatment, blasting treatment, acid treatment with acidic solutions such as sulfuric acid, alkali treatment with alkali solutions such as sodium hydroxide, treatment with ammonia ($NH_3$), enzyme treatment, and treatment with compounds containing an amino group ($NH_2$). Among these pieces of pretreatment, the pretreatment step pretreats the cellulose-based biomass using the ammonia-containing treating agent. Although it has been known that the pretreatment of the cellulose-based biomass produces coumaric acid, it has not been confirmed that the cellulose-based biomass pretreated with the ammonia-containing treating agent produces coumaramide. We believe that the pretreatment with the ammonia-containing treating agent amidates coumaric acid originated from the cellulose-containing biomass to produce coumaramide.

The ammonia-containing treating agent used in the pretreatment step may be, other than ammonia, an amino group-containing compound. Ammonia or the amino group-containing compound and a plurality of other compounds may be used in combination. Examples of the amino group-containing compound include methylamine, ethylamine, propylamine, butylamine, hydrazine, ethylenediamine, propanediamine, and butanediamine. Examples of the other compounds include carbon dioxide, nitrogen, ethylene, methane, ethane, propane, ethane, butane, pentane, hexane, toluene, benzene, phenol, dioxane, xylene, acetone, chloroform, carbon tetrachloride, ethanol, methanol, propanol, and butanol.

The ammonia-containing treating agent may be any of liquid, gas, and a gas-liquid mixed phase. Ammonia in the state of any of liquid, gas, and a gas-liquid mixed phase can produce cellulose-based biomass having excellent enzymatic saccharification efficiency. The ammonia-containing treating agent may be a supercritical ammonia fluid or a subcritical ammonia fluid. Examples of a method of treatment using the supercritical ammonia fluid include, but not limited to, introducing cellulose-based biomass and ammonia into a reaction vessel such as an autoclave, heating and pressurizing the inside of the reaction vessel, and putting the ammonia into a supercritical state.

Harvested cellulose-based biomass may be used at the pretreatment step as it is. The cellulose-based biomass may be put into particles of cellulose-based biomass having an average particle diameter of a certain size or less by cutting, crushing, or the like to be used at the pretreatment step. Reducing the particle diameter of the cellulose-based biomass in advance can facilitate handling and improve treatment efficiency by the ammonia-containing treating agent.

The particle diameter of the particles of the cellulose-based biomass can be appropriately selected without specific limitations. For example, it is preferably 5 mm in diameter or less, more preferably 1 mm in diameter or less, and further preferably 0.1 mm in diameter or less. If the particle diameter of the particles of the cellulose-based biomass exceeds 5 mm, the elution of coumaramide into water can be insufficient at the extraction step described below. If the particle diameter of the particles of the cellulose-based biomass is within the above range, coumaramide can be sufficiently eluted into water, and the use amount of the ammonia-containing treating agent can be reduced.

Although the harvested cellulose-based biomass may be treated with the ammonia-containing treating agent as it is, that is not limiting. From the viewpoint of collecting the ammonia-containing treating agent used at the pretreatment step, the cellulose-based biomass may be dried to be used at the pretreatment step.

Although the method that treats the cellulose-based biomass with the ammonia-containing treating agent is used as the method of pretreatment, the above methods of pretreatment for the cellulose-based biomass may be used in combination.

(2) Coumaramide Extraction Step

In the extraction step, the ammonia-treated biomass obtained at the pretreatment step is immersed into the solvent to elute coumaramide in the ammonia-treated biomass into the solvent. At the extraction step, the solvent for use in the elution of coumaramide from the ammonia-treated biomass contains at least water. When an organic solvent such as pure ethanol or acetonitrile that contains no water is used as the solvent, almost no coumaramide is eluted. The coumaramide originated from the cellulose-based biomass is covered with water-soluble compounds such as cellooligosaccharide, xylooligosaccharide, and pectin. We believe that coumaramide is not extracted because these compounds are insoluble in organic solvents. However, the real reason is not clear. Examples of the water for use in the extraction of coumaramide preferably include, but not limited to, pure water, tap water, industrial water, river water, and rainwater. Another preferable water is water obtained by reclaiming a residue after collecting coumaramide by reverse osmosis membrane treatment described below.

The solvent used at the extraction step may contain a polar organic solvent in addition to water. The solvent containing the polar organic solvent in addition to water has the effect of increasing the extraction amount of coumaramide. Examples of the polar organic solvent include ethanol, acetonitrile, methanol, 1-propanol, 2-propanol, ethylene glycol, acetone, acrylonitrile, dimethylsulfoxide, and dimethylformamide. The solvent may contain one or two or more solvents of the above polar organic solvents, preferably contains at least ethanol or acetonitrile, and more preferably contains ethanol. The solvent for use in the extraction of coumaramide preferably contains the polar organic solvent in a ratio of 1% by volume to 50% by volume. This is because if the ratio of the polar organic solvent in the solvent is less than 1% by volume, the effect of increasing the extraction amount of coumaramide may be insufficient, and if the ratio exceeds 50% by volume, the concentration of the polar organic solvent increased thereabove not only does not increase the extraction amount of coumaramide but also can extract water-insoluble components in the biomass such as lignin and decrease the purity of coumaramide. In the crystallization step described below, when coumaramide is further purified by filtration through a nanofiltration membrane described below or when it is further concentrated by filtration through a reverse osmosis membrane described below before crystallization, the concentration of the polar organic solvent contained in water is preferably 1% by volume to 10% by volume. The concentration exceeding 10% by volume can damage the nanofiltration membrane or the reverse osmosis membrane by the polar organic solvent.

At the extraction step, when the ammonia-treated biomass is immersed into the solvent, the ammonia-treated biomass may be hydrolyzed by appropriately adding a diastatic enzyme. The ammonia-treated biomass is extracted while being hydrolyzed by the diastatic enzyme, thereby enabling the coumaramide present within the biomass to be extracted and the yield of the coumaramide to be increased.

The diastatic enzyme (cellulase) is a generic name for enzymes having activity that decomposes cellulose and/or hemicellulose, especially xylan, and can be exemplified by cellobiohydrolase, endoglucanase, exoglucanase, β-glucosidase, xylanase, β-xylosidase, and xyloglucanase. The cellulase may be general cellulase and is preferably a diastatic enzyme including cellobiohydrolase having decomposition activity for crystalline cellulose or endoglucanase. Such a diastatic enzyme is preferably a diastatic enzyme originated from Trichoderma fungi. The Trichoderma fungi are microorganisms classified into filamentous fungi and are microorganisms that extracellularly secrete a large amount of many kinds of cellulase.

At the extraction step, examples of the method of immersing the ammonia-treated biomass into the solvent include, but not limited to, performing mixing with stirring and leaving at rest, and performing mixing with stirring is preferable, because it can extract coumaramide more efficiently. When performing the biomass hydrolysis through the addition of cellulase in particular, performing mixing with stirring is preferable, because the efficiency of biomass hydrolysis is increased, and the extraction efficiency of coumaramide is more increased.

At the extraction step, examples of an immersion time of the ammonia-treated biomass into the solvent are preferably, but not limited to, 1 minute to 60 minutes. This is because if the immersion time is less than 1 minute, the extraction of coumaramide may be insufficient, and if the immersion time exceeds 60 minutes, taking more time does not increase the extraction efficiency of coumaramide. However, when performing the biomass hydrolysis through the addition of the diastatic enzyme at the extraction step, cellulose and hemicellulose in the ammonia-treated biomass are decomposed with time, and more coumaramide is eluted into the liquid. In view of this, it is preferable that the immersion time be from 2 hours to 24 hours to sufficiently hydrolyze the ammonia-treated biomass.

At the extraction step, examples of a temperature when the ammonia-treated biomass is immersed into the solvent to extract coumaramide are preferably, but not limited to, 40° C. to 80° C. This is because coumaramide is extracted significantly efficiently at a temperature of 40° C. or higher. Although it is inferred that lignin, tannin, polysaccharide, oligosaccharide, or the like surrounding the coumaramide in the ammonia-treated biomass is dissolved or liberated at the temperature, the real reason is not clear. Even if the temperature exceeds 80° C., the extraction efficiency of coumaramide is not increased, and if the temperature exceeds 100° C., polysaccharide, lignin, or the like in the ammonia-treated biomass is decomposed by heat, producing impurities such as hydroxymethyl furfural (HMF), furfural, formic acid, acetic acid, and vanillin, which is not preferable.

Examples of the amount the solvent for use in the extraction of coumaramide are preferably, but not limited to, from 2 kg to 30 kg with respect to 1 kg of the ammonia-treated biomass in terms of dry mass. If the amount of the solvent for use in the extraction is within the range of from 2 kg to 30 kg with respect to 1 kg of the ammonia-treated biomass in terms of dry mass, the coumaramide in the ammonia-treated biomass can be sufficiently extracted. If the amount of the solvent for use in the extraction is less than 2 kg with respect to 1 kg of the ammonia-treated biomass in terms of dry mass, the coumaramide in the ammonia-treated biomass may not be sufficiently extracted, and almost all of the solvent (water) may be absorbed into the ammonia-treated biomass, which sometimes makes it difficult to collect the coumaramide solution. If the amount of the solvent for use in the extraction exceeds 30 kg with respect to 1 kg of the ammonia-treated biomass in terms of dry mass, even any amount of the solvent increased thereabove not only has no effect on the extraction amount of coumaramide but also increases the amount of the solvent treated when concentrating coumaramide in the crystallization step described below, which is economically disadvantageous.

(3) Crystallization Step

At the crystallization step, the coumaramide in the coumaramide solution obtained at the extraction step is put into a supersaturated state, thereby precipitating a coumaramide crystal and collecting the coumaramide. Crystallization generally indicates a method that precipitates and grows a solute and collects it as a crystalline by making a solution state in which the solute is dissolved in an extent exceeding its solubility, that is, a supersaturated state by increasing the concentration of the solute, decreasing the solubility of the solute, combining these, or the like. Examples of a general method of crystallization include methods that increase the concentration of the solute such as heating evaporation, vacuum drying, and freeze drying; and methods that decreases the solubility such as cooling, chemical reactions, and pressurizing. The method of crystallization at the crystallization step can use these methods without special limitations. The coumaramide solution obtained at the extraction step contains a large amount of solids, and these solids are preferably removed before the crystallization of coumaramide. Example of a method of removing the solids include, but not limited to, centrifugation, filter press, belt filters, microfiltration, and mesh screens, filtration by unwoven cloth, and any combination thereof. Among the above, microfiltration can remove micron-order particles to increase the purity of coumaramide at crystallization, and it is preferable to perform microfiltration at the final stage of the removal of the solids.

At the crystallization step, before precipitating the crystal from the coumaramide solution, it is preferable to perform a concentration step of concentrating the coumaramide solution in advance. Examples of a method of concentrating the coumaramide solution include, but not limited to, membrane separation, which can perform high concentration with saved energy, that is, a method that filtrates the coumaramide solution through a membrane and concentrates the coumaramide on the non-permeate side. When concentrating the coumaramide by membrane separation, if a coumaramide crystal is precipitated during membrane separation, the membrane becomes clogged, and it is preferable to control not to precipitate the coumaramide during membrane separation.

A reverse osmosis membrane can be used as a separation membrane that concentrates coumaramide by membrane separation. The reverse osmosis membrane is also called an RO membrane and is a membrane generally defined as "a membrane having a demineralization ability including univalent ions." The reverse osmosis membrane is a membrane that is believed to have ultrasmall voids having a size of from several angstroms to several nanometers and is mainly used for ion component removal such as desalination and ultrapure water manufacture. Coumaramide is blocked on the non-permeate side, while removing water on the permeate side, thereby enabling the reverse osmosis membrane to be used for the purpose of concentrating the coumaramide solution. The water removed on the permeate side when the coumaramide solution is concentrated contains few impurities, and it can be reused for various uses. For example, it can be used as the solvent for use in the above coumaramide extraction step. The reverse osmosis membrane that may be used is the one disclosed in WO2010/067785, for example.

Examples of the shape of the reverse osmosis membrane for use in the concentration of the coumaramide solution include, but are not limited to, shapes of a hollow fiber membrane module, a flat membrane, and a spiral module, and among them, the shape of the spiral module is preferable because the spiral module can highly concentrate coumaramide due to its generally high pressure resistance and has a large treatment amount due to its large effective membrane area.

The temperature of the coumaramide solution when concentrating coumaramide using the reverse osmosis membrane is preferably 20° C. to 50° C. If the temperature is 20° C. or higher, coumaramide is unlikely to be precipitated, thus producing no membrane clogging. If the temperature is lower than 20° C., coumaramide is significantly likely to be precipitated, thus being likely to produce membrane clogging. If the concentration of coumaramide is continued at a temperature exceeding 50° C., the deterioration of the membrane may be accelerated.

The above general crystallization methods can be used for crystallization of the coumaramide solution after concentrating the coumaramide solution, and among them, cooling is preferably used. This is because when performing crystallization by the cooling of the coumaramide solution, high-purity coumaramide can be collected with a favorable yield at a relatively moderate cooling temperature. Although this may be because the temperature dependence of the solubility of coumaramide is higher than the other substances extracted from the ammonia-treated biomass, the reason is not clear.

At the crystallization step, the temperature of the cooling of the coumaramide solution is preferably 15° C. or lower. This is because if the temperature is 15° C. or lower, the precipitation and growth of the coumaramide crystal are remarkable.

At the crystallization step, examples of a cooling period are preferably, but not limited to, from 5 hours to 10 days. If the cooling period is less than 5 hours, the precipitation and growth of the coumaramide crystal are poor, thus reducing the collection amount of coumaramide. If the cooling period exceeds 10 days, almost no more crystal is precipitated and grows, thus not increasing the collection amount of coumaramide, which is not preferable.

At the crystallization step, before crystallization of coumaramide or concentration of the coumaramide solution by the reverse osmosis membrane, a purification step may be performed by filtrating the coumaramide solution through a nanofiltration membrane and obtaining a purified coumaramide solution as a permeate. Performing the purification step can remove impurities from the coumaramide solution and increase the purity of the coumaramide crystal obtained at crystallization. The nanofiltration membrane is also called a nanofilter (a nanofiltration membrane, an NF membrane) and is a membrane generally defined as "a membrane that filtrates univalent ions and blocks divalent ions." The nanofiltration membrane is a membrane considered to have microscopic voids having a size of several nanometers and is mainly used to block micro-particles, molecules, ions, salts, or the like in water. By subjecting the coumaramide solution to the nanofiltration membrane, impurities originated from the biomass including sugars are blocked on the non-permeate side, whereas the coumaramide solution is filtrated to the permeate side, thereby purifying the coumaramide solution. The nanofiltration membrane may be the one disclosed in WO2010/067785, for example.

Examples of the shape of the nanofiltration membrane include, but are not limited to, similar shapes to those of the above reverse osmosis membrane.

The coumaramide crystal obtained by crystallization is collected by solid-liquid separation. Examples of the method of solid-liquid separation include, but not limited to, centrifugation, filter press, microfiltration, and mesh screens, filtration by unwoven cloth, filtration by filter paper, and any combination thereof.

At the crystallization step, the purity of the collected coumaramide crystal is preferably 90% or higher, more preferably 95% or higher, and further preferably 97% or higher.

At the crystallization step, even if the coumaramide crystal collected by solid-liquid separation is dried as it is, high purity of 90% or higher can be obtained, and washing with water can further improve the purity. This is because coumaramide has poor solubility to water, and washing with water preferentially removes water-soluble impurities. Examples of the temperature at washing with water are preferably, but not limited to, 5° C. to 20° C. This is because if the temperature is lower than 5° C., the water-soluble impurities are not sufficiently removed due to the poor solubility of the water-soluble impurities, and if the temperature exceeds 20° C., the solubility of coumaramide increases, and the yield of coumaramide decreases. The purity of the coumaramide crystal can be measured by a method of Reference Example 2 of Examples described below.

Crushing the coumaramide crystal before washing it with water can further increase the efficiency of removing the impurities. Examples of the method of crushing include, but not limited to, hammer mills, wing mills, ball mills, stone mills, mortars, and any combination thereof.

The coumaramide crystal after washing it with water is recollected by the above solid-liquid separation or the like. The above washing with water, crushing, and collection by solid-liquid separation may be appropriately combined or repeated. Repeating them can further increase the purity of the coumaramide crystal.

EXAMPLES

Reference Example 1

HPLC Analysis Conditions

In the examples, the concentrations of organic acids and aromatic compounds in a solution were analyzed under the following HPLC conditions.
(1) Organic Acid Analysis Conditions
The concentration of acetic acid in the solution was quantified by comparison to an authentic sample under the following HPLC conditions:
Instrument: Hitachi High Speed Liquid Chromatograph Lachrom elite (manufactured by Hitachi, Ltd.)
Column: GL-C610H-S (manufactured by Hitachi, Ltd.)
Mobile phase: 3 mM perchloric acid
Reaction liquid: bromothymol blue solution
Method of detection: UV-VIS detector
Flow rate mobile phase: 0.5 mL/min Reaction liquid: 0.6 mL/min
Temperature: 60° C.
(2) Aromatic Compound Analysis
The concentration of the aromatic compounds (coumaric acid, coumaramide, and ferulamide) in the solution was quantified by comparison with authentic samples under the following HPLC conditions. At the same time, UV absorption spectra (measurement wavelength: from 200 nm to 400 nm) of respective detection peaks were obtained.
Instrument: Hitachi High Speed Liquid Chromatograph Lachrom elite (manufactured by Hitachi, Ltd.)
Column: Synergi 2.5 μm Hydro-RP 100A (manufactured by Phenomenex Inc.)
Method of detection: Diode Array detector
Flow rate: 0.6 mL/min
Temperature: 40° C.

Reference Example 2

Measurement of Purity and Yield of Coumaramide

The total amount of the coumaramide crystal obtained at the crystallization step was vacuum dried at 5 kPa for 6 hours to obtain a dry coumaramide crystal. The total amount of the dry coumaramide crystal was thoroughly mashed with a mortar and was further vacuum dried at 5 kPa during a whole day and night to obtain dry coumaramide powder. The mass of the total amount of the dry coumaramide powder was measured by an electronic balance, and then part, or 1,000 mg, of the dry coumaramide powder was measured by a precision balance and was dissolved into a 50% by volume acetonitrile/water mixed solution, to which the 50% by volume acetonitrile/water mixed solution was added in a 500 mL measuring flask up to a marked line. After analyzing the concentration of coumaramide in a solution obtained by diluting the obtained solution 20 times with pure water in accordance with Reference Example 1, the purity of coumaramide was calculated in accordance with the following Expression (1). The yield of coumaramide was calculated in accordance with the following Expression (2). The dry mass of charged biomass means the dry mass of the entire ammonia-treated biomass served at the extraction step.

Purity of coumaramide (%)=measured value of concentration of coumaramide (mg/L)/100 (mg/L)× 100 (1)

Yield of coumaramide (mg/kg)=mass of dry coumaramide powder (mg)×purity of coumaramide (%)/(dry mass of charged biomass (kg)×100) (2)

Example 1

Manufacture and Identification of Coumaramide Crystal

A. Preparation of Crystal of Ammonia-Treated Biomass Extract
(1) Pretreatment Step
(1.1) Pulverization Treatment on Cellulose-Based Biomass
Erianthus was used as the cellulose-based biomass. The erianthus was crushed by a cutter mill while controlling its particle size by a screen having a mesh size of 4 mm. The average diameter (d50) measured by the laser diffraction method was about 975 μm. The crushed erianthus was dried at a temperature of 40° C. at a reduced pressure of 5 kPa during a whole day and night. The water content of the dried erianthus was about 0.5% by mass based on the mass of the dried erianthus.
(1.2) Treatment on Cellulose-Based Biomass with Ammonia-Containing Treating Agent
The crushed and dried erianthus (cellulose chips) obtained in (1.1) was pretreated with ammonia as an ammonia-containing treating agent. A stainless steel autoclave having an inner capacity of about 5 L and equipped with a stirring device was filled with 200 g of the cellulose chips. Introduction of pressurized nitrogen gas into the autoclave and degassing were repeated to remove air within the autoclave and replace the air with the nitrogen gas. The temperature of the autoclave was then raised up to 120° C. After the temperature rise, the inside of the autoclave was degassed, and further its pressure was reduced to discharge the nitrogen gas. Meanwhile, pressurized ammonia was introduced into a separate pressure vessel, and the temperature of the ammonia was raised up to a temperature slightly above 120° C. By opening a valve installed in a pipe connecting between the autoclave and the pressure vessel, the ammonia was introduced into the autoclave to give a pressure of 1.2 MPa at a temperature of 120° C. Under this temperature and pressure conditions, the cellulose chips were treated with stirring for 2.5 hours. The ammonia was then discharged by degassing, and in addition, nitrogen gas was circulated through the autoclave to remove ammonia remaining in the cellulose chip particles to obtain pretreated biomass, which was used as the ammonia-treated biomass.

(2) Extraction Step

Nine kilograms of water as an extractant was added to 1 kg of the ammonia-treated biomass in terms of dry mass, and the mixture was stirred at 20° C. for 30 minutes. The stirred suspension was used at the following step as an ammonia-treated biomass extract.

Crystallization Step (3.1) Purification and Concentration

Solids contained in the ammonia-treated biomass extract obtained in (2) extraction step was removed by filter press treatment (MO-4 manufactured by Yabuta Industries Co., Ltd.) to perform the purification step. By subjecting the ammonia-treated biomass extract to a microfiltration membrane having a pore diameter of 0.22 μm, micron-order insoluble impurities were removed. For the thus obtained liquid, its solvent was evaporated until the liquid amount became about half to perform the concentration step (heating evaporation).

(3.2) Crystallization

After leaving the ammonia-treated biomass extract concentrated in (3.1) at rest at 15° C. for 1 day, crystal precipitation was observed. The crystal was separated by a sieve having a mesh size of 500 μm. One liter of water was added to the thus obtained crystal, and the mixture was suspended at room temperature and was separated again by the sieve having a mesh size of 500 μm. The obtained crystal was dried at 50° C. during a whole day and night and was further vacuum dried at 10 kPa for about 6 hours to obtain a dry crystal.

B. Identification of Ammonia-Treated Biomass Extract

Figure 2:
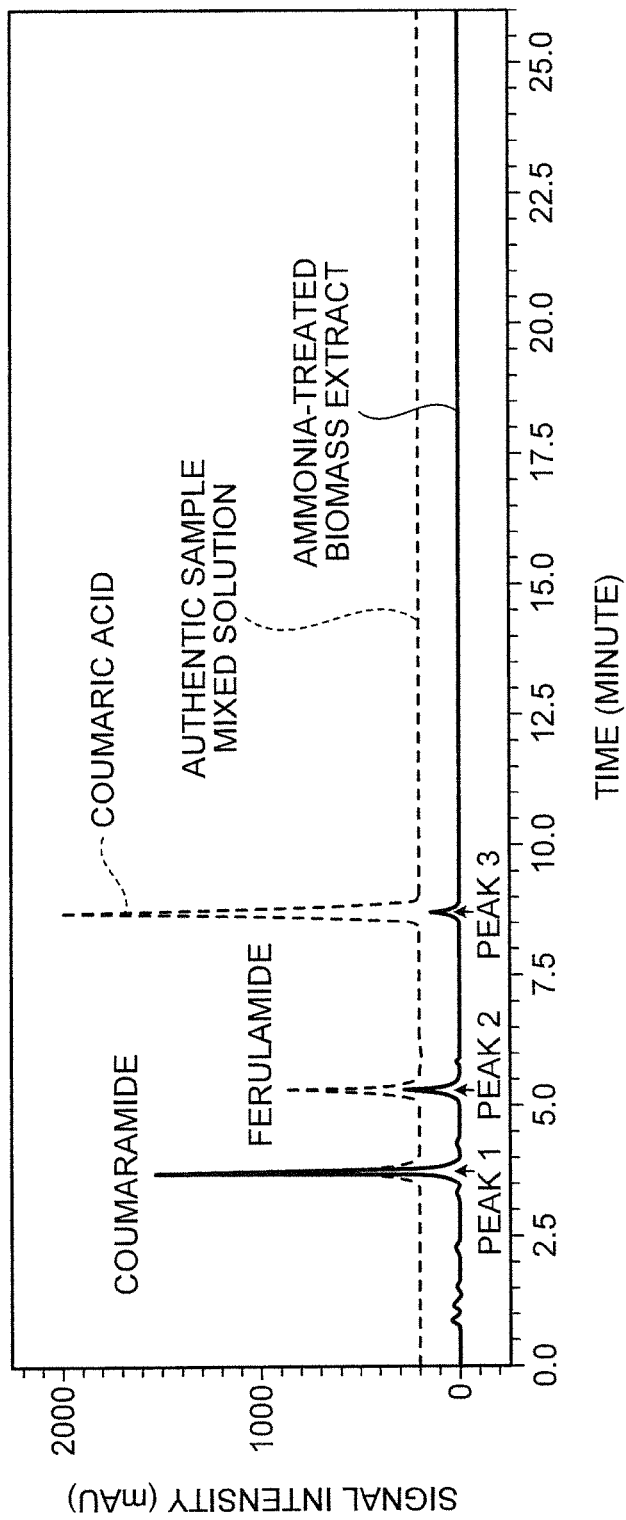
FIG. 2 is a diagram illustrating a result of analyzing aromatic compounds in an ammonia-treated biomass extract by HPLC.

As a result of analyzing the ammonia-treated biomass extract obtained in (2) extraction step under the HPLC conditions described in the organic acid analysis conditions of Reference Example 1, we found that acetic acid was contained as a principal organic acid component. Similarly, as a result of analyzing the ammonia-treated biomass extract under the HPLC conditions described in the aromatic compound analysis conditions of Reference Example 1, three principal peaks (Peak 1, Peak 2, and Peak 3) were detected as illustrated in FIG. 2.

Among these, Peak 3 was identified to be coumaric acid, because its HPLC elution time matched that of an authentic sample of coumaric acid. The elution times of the two residual compounds (Peak 1 and Peak 2) did not match any of authentic samples of hydroxymethyl furfural (HMF), furfural, vanillin, apocynin, ferulic acid, coniferyl aldehyde, and guaiacol known as aromatic compounds contained in a cellulose-based biomass pretreated product. Given these circumstances, these two peaks (Peak 1 and Peak 2) were fractionated by HPLC to analyze their molecular weight by LC/MS (LCMS-IT-TOF and LC20A manufactured by Shimadzu Corporation).

As a result of the analysis, we found that the molecular weights thereof were 163.063 and 193.074. It is known that various pieces of biomass contain coumaric acid and ferulic acid, and they are expected to undergo a condensation reaction with an ammonia molecule to produce coumaramide and ferulamide, respectively. The molecular weights calculated from the structural formulae of coumaramide and ferulamide are 163.172 and 193.198, respectively, which match the molecular weights obtained by LC/MS, and it was estimated that the two residual peaks (Peak 1 and Peak 2) contained in the ammonia-treated biomass extract were coumaramide and ferulamide.

Given these circumstances, authentic samples of coumaramide and ferulamide were entrusted to be synthesized (company entrusted: Synthesis Laboratory, VSN, Inc.). The synthesized authentic samples were analyzed under the HPLC conditions described in the aromatic compound analysis conditions of Reference Example 1, and elution times were measured. As a result of the measurement, Peak 1 in the ammonia-treated biomass extract and Peak 2 in the ammonia-treated biomass extract perfectly matched the elution time (3.74 minutes) of the authentic sample of coumaramide in an authentic sample mixed solution and the elution time (5.25 minutes) of the authentic sample of ferulamide in the authentic sample mixed solution, respectively (refer to FIG. 2).

Figure 3:
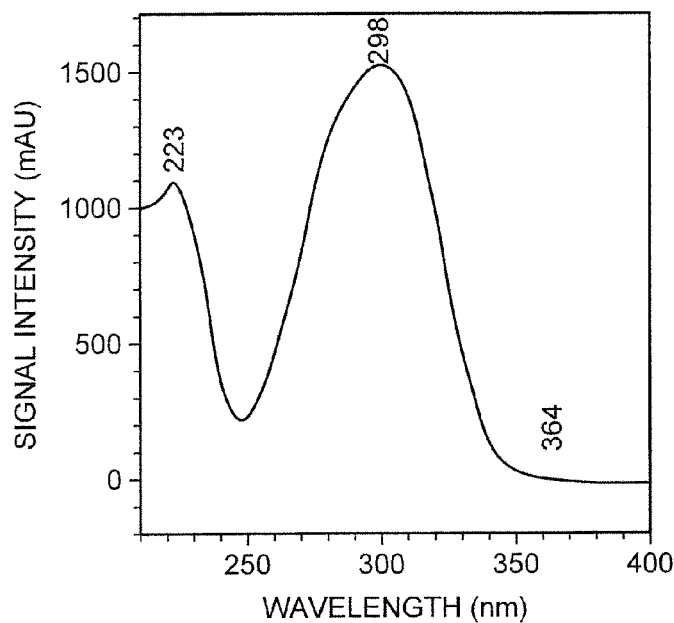
FIG. 3 is a diagram illustrating a UV absorption spectrum of Peak 1 of the ammonia-treated biomass extract.
Figure 4:
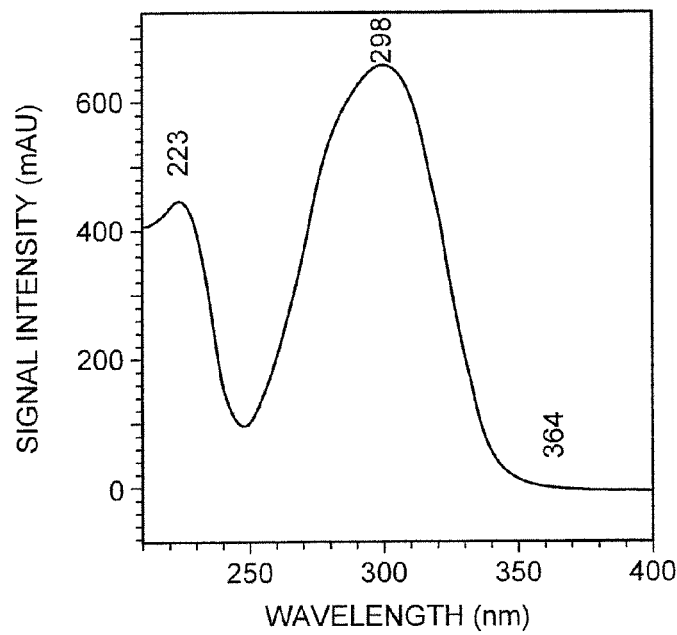
FIG. 4 is a diagram illustrating a UV absorption spectrum of an authentic sample of coumaramide.
Figure 5:
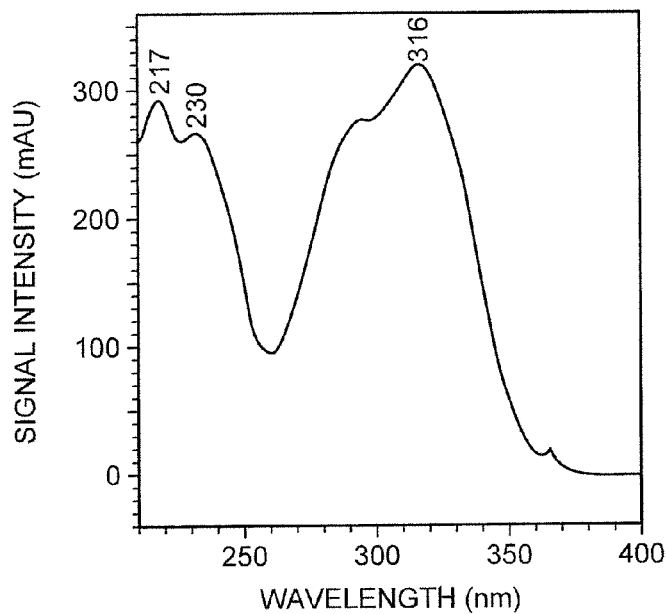
FIG. 5 is a diagram illustrating a UV absorption spectrum of Peak 2 of the ammonia-treated biomass extract.
Figure 6:
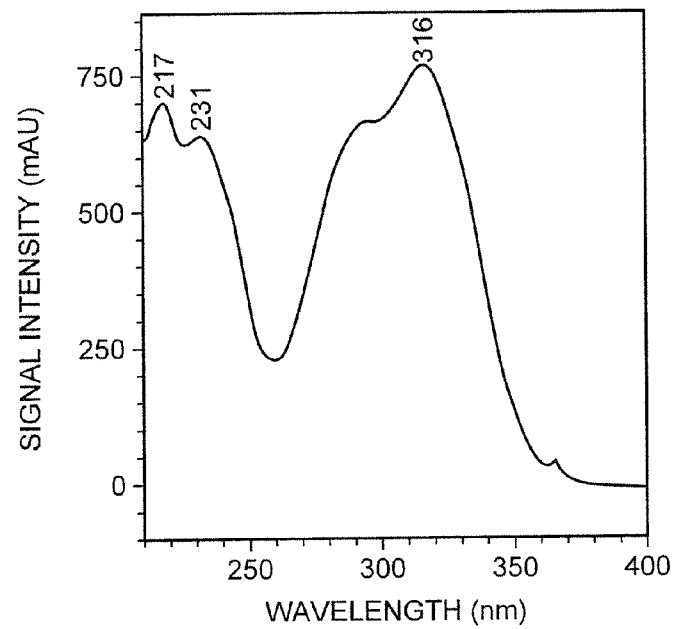
FIG. 6 is a diagram illustrating a UV absorption spectrum of an authentic sample of ferulamide.

FIGS. 3 to 6 illustrate UV absorption spectra of Peak 1 and Peak 2 in the ammonia-treated biomass extract obtained when HPLC was performed, the authentic sample of coumaramide, and the authentic sample ferulamide. The measurement wavelengths were set at from 200 nm to 400 nm. As illustrated in FIGS. 3 and 4, the UV spectra of Peak 1 in the ammonia-treated biomass extract and the authentic sample of coumaramide matched each other. As illustrated in FIGS. 5 and 6, the UV spectra of Peak 2 in the ammonia-treated biomass extract and the authentic sample of ferulamide matched each other.

From the foregoing analysis results, we found that Peak 1 and Peak 2 contained in the ammonia-treated biomass extract were coumaramide and ferulamide, respectively, and that the ammonia-treated biomass extract contained a large amount of these compounds. Table 1 lists a result of component analysis on the ammonia-treated biomass extract.

TABLE 1

| Components of ammonia-treated biomass extract | | | | |
| --- | --- | --- | --- | --- |
| Acetic acid (mg/L) | Coumaric acid (mg/L) | Ferulic acid (mg/L) | Coumaramide (mg/L) | Ferulamide (mg/L) |
| 320 | 36 | 25 | 383 | 240 |

As a result of analyzing a 50% by volume acetonitrile/water mixed solution dissolving the crystal obtained at (3) the crystallization step in a proper amount on the HPLC conditions described in the aromatic compound analysis conditions of Reference Example 1, a single peak was obtained, and its elution time matched that of coumaramide. The UV spectrum of the peak obtained in the HPLC analysis matched the UV spectrum of the authentic sample of coumaramide. From the foregoing, it was found that the crystal obtained in (3) crystallization step was a coumaramide crystal. Table 2 lists results of the analysis of the purity and yield of the coumaramide crystal in accordance with Reference Example 2.

TABLE 2

| | Enzymatic saccharification* | Nano-filtration* | Method of Concentration | Purity of coumaramide | Yield of coumaramide mg/kg-raw material |
| --- | --- | --- | --- | --- | --- |
| Example 1 | – | – | Heating evaporation | 92.2% | 254 |
| Example 2 | – | – | Reverse osmosis | 92.4% | 920 |

TABLE 2-continued

|  | Enzymatic saccharification* | Nano-filtration* | Method of Concentration | Purity of coumaramide | Yield of coumaramide mg/kg-raw material |
|---|---|---|---|---|---|
| Example 5 | − | + | membrane filtration Reverse osmosis membrane filtration | 97.3% | 914 |
| Example 6 | + | − | Reverse osmosis membrane filtration | 91.9% | 1230 |

*In the table, + indicates the processing was performed, wherein − indicates the processing was not performed.

Example 2

Coumaramide Concentration by Reverse Osmosis Membrane

An ammonia-treated biomass extract was purified in the same manner as Example 1 until (1) the pretreatment step, (2) the extraction step, and the purification step in (3.1) the purification and concentration step. The obtained liquid was filtrated at 25° C. using a reverse osmosis membrane (UTC-80 manufactured by Toray Industries, Inc.) to concentrate the ammonia-treated biomass extract. The filtration was performed by appropriately adjusting the operation pressure so that the membrane permeable flux in the cross flow filtration was 0.5 m/day and was ended when the liquid was concentrated to be nearly halved in amount. After cooling the obtained concentrate to 15° C. and leaving it at rest for 1 day, crystal precipitation was observed. The crystal was separated by a sieve having a mesh size of 500 μm. One liter of water was added to the thus obtained crystal, and the mixture was suspended at room temperature and was separated again by the sieve having a mesh size of 500 μm. The obtained crystal was dried at 50° C. during a whole day and night and was further vacuum dried at 10 kPa for about 6 hours to obtain a dry coumaramide crystal. Table 2 lists results of the analysis of the purity and yield of the obtained coumaramide crystal by the method described in Reference Example 2. Table 2 provides a summary of the purity and yield of coumaramide by differences at the extraction step, the purification step, and the concentration step. As is evident from Table 2, the coumaramide concentration performed by the reverse osmosis membrane increased the yield of coumaramide compared to the heating evaporation.

Example 3

Extraction of Coumaramide with Hot Water

Ammonia-treated biomass extracts were obtained by a similar method to (1) the pretreatment step and (2) the extraction step in Example 1 except that the temperature of the extraction step was varied to be 10° C., 20° C., 30° C., 40° C., 50° C., 70° C., and 90° C. Table 3 lists results of component analysis under the HPLC conditions described in Reference Example 1 on the ammonia-treated biomass extracts extracted at the respective temperatures. As is evident from Table 3, a higher temperature at extraction gave a higher concentration of coumaramide in the biomass extract; at lower than 40° C., the extraction concentration was poor, whereas at 40° C. or higher, the extraction concentration was significantly increased. The extraction concentration reached nearly its upper limit at 70° C. and did not increase any more even at a temperature increased thereabove.

TABLE 3

|  | Temperature at extraction (° C.) | | | | | | |
|---|---|---|---|---|---|---|---|
|  | 10 | 20 | 30 | 40 | 50 | 70 | 90 |
| Concentration of coumaramide (mg/L) | 310 | 383 | 510 | 954 | 1150 | 1223 | 1230 |

Example 4

Extraction of Coumaramide with Solvent Containing Polar Organic Solvent

Ammonia-treated biomass extracts were obtained by a similar method to (1) the pretreatment step and (2) the extraction step in Example 1 except that a 10% ethanol aqueous solution and a 10% acetonitrile aqueous solution were used as extractants. Table 4 lists results of component analysis under the HPLC conditions described in Reference Example 1 on the ammonia-treated biomass extracts extracted with the respective extractants. Table 4 provides a summary of the concentration of coumaramide in the ammonia-treated biomass extracts when using different extractants.

TABLE 4

|  |  | Example 4 | | Comparative Example 1 | |
|---|---|---|---|---|---|
| Extractant | Example 1 Pure water | 10% Ethanol | 10% Aceto-nitrile | Pure ethanol | Pure aceto-nitrile |
| Concentration of coumaramide (mg/L) | 383 | 634 | 520 | 25 | 18 |

Comparative Example 1

Extraction of Coumaramide with Pure Organic Solvent

Ammonia-treated biomass extracts were obtained by a similar method to (1) the pretreatment step and (2) the extraction step in Example 1 except that pure ethanol and pure acetonitrile were used as extractants. Table 4 lists results of component analysis under the HPLC conditions described in Reference Example 1 on the ammonia-treated biomass extracts extracted with the respective extractants. As is evident from Table 4, Example 4, which used 10% ethanol or 10% acetonitrile, gave an increased concentration of coumaramide compared to Example 1, which used pure water as the extractant, and in particular, that effect was remarkable for ethanol. Reference Example 1, which used pure ethanol or acetonitrile, collected almost no coumaramide.

Example 5

Purification of Coumaramide by Nanofiltration Membrane

A dry coumaramide crystal was obtained by a similar method to Example 2 except that coumaramide was purified by filtrating a solid-removed ammonia-treated biomass extract by filter press and a microfiltration membrane before concentration by a reverse osmosis membrane and further performing filtration using a nanofiltration membrane (UTC-80 manufactured by Toray Industries, Inc.) at 25° C. The filtration by the nanofiltration membrane was performed by appropriately adjusting the operation pressure so that the membrane permeable flux in the cross flow filtration was 0.5 m/day and was ended when the operation pressure reached 6 MPa. Table 2 lists results of the analysis of the purity and yield of the obtained coumaramide crystal by the method described in Reference Example 2. As is evident from Table 2, Example 5, which performed the purification of coumaramide by the nanofiltration membrane, gave an increased purity of the coumaramide crystal compared to Example 2, which did not perform the purification of coumaramide by the nanofiltration membrane.

Example 6

Enzymatic Saccharification in Extraction Step

Nine kilograms of water was added to 1 kg of the ammonia-treated biomass in terms of dry mass obtained by the method described in (1) the pretreatment step in Example 1. A small amount of concentrated sulfuric acid was added thereto to adjust pH to be 5. A cellulase preparation originated from *Trichoderma ressei* (Accellerase DUET manufactured by Genencor, Inc.) as a diastatic enzyme was added thereto in an amount of one hundredth in terms of the mass of enzyme protein with respect to the dry mass of the ammonia-treated biomass to cause a saccharification reaction by stirring at 50° C. for 24 hours. The obtained suspension, as an ammonia-treated biomass extract, was treated (purification, concentration, and crystallization) in a similar manner to the method described in Example 2 to obtain a dry coumaramide crystal.

Figure 7:
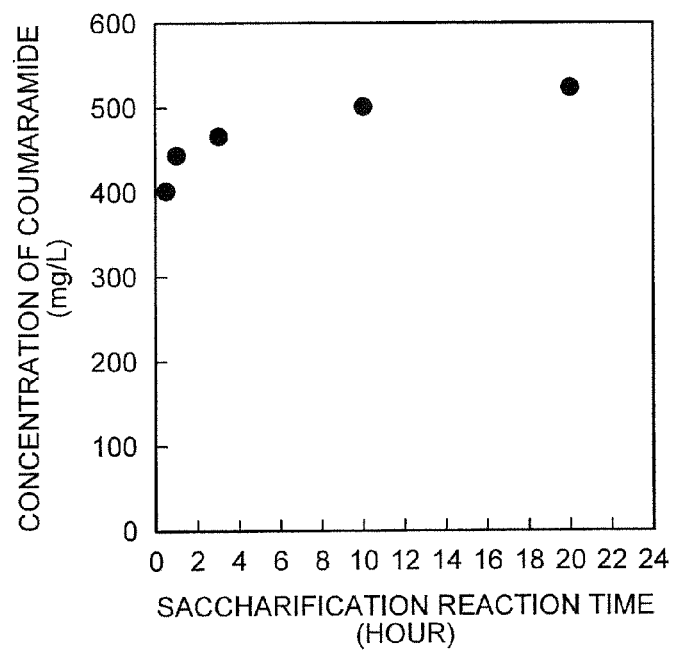
FIG. 7 is a diagram illustrating changes with time of the concentration of coumaramide contained in a supernatant of a reaction liquid during a saccharification reaction.

FIG. 7 illustrates a result of the analysis of changes with time of the concentration of coumaramide contained in a supernatant of a reaction liquid during the saccharification reaction in accordance with Reference Example 1. As is evident from FIG. 7, as the saccharification reaction proceeds, the concentration of coumaramide in the solution increased.

Table 2 lists results of the analysis of the purity and yield of the obtained dry coumaramide crystal by the method described in Reference Example 2. As is evident from Table 2, Example 6, which performed the enzymatic saccharification at the extraction step, gave an increased yield of coumaramide compared to Example 2, which did not perform the enzymatic saccharification.

Example 7

Immersion Time

Figure 8:
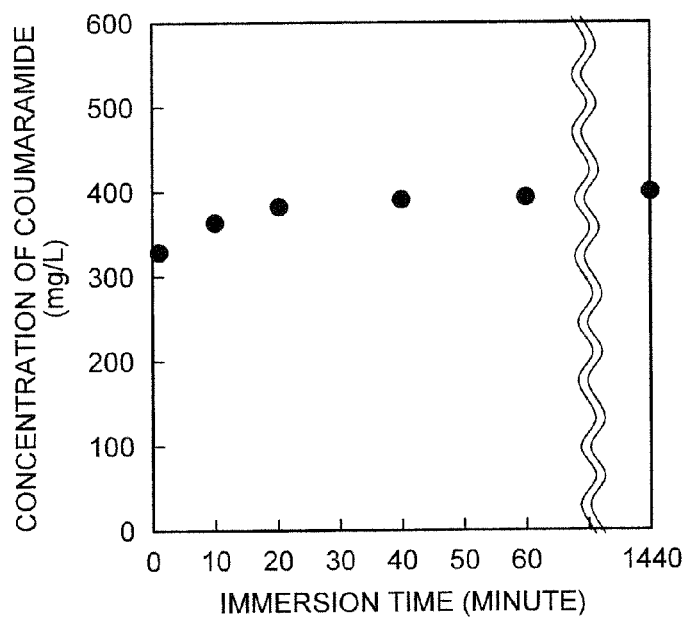
FIG. 8 is a diagram illustrating changes with time of the concentration of coumaramide contained in a supernatant of a suspension in an extraction step.

Extraction of coumaramide from the ammonia-treated biomass was performed in a similar method to (1) the pretreatment step and (2) the extraction step in Example 1 except that the stirring time was 24 hours. FIG. 8 illustrates a result of the analysis of changes with time of the concentration of coumaramide contained in a supernatant of a suspension during extraction in accordance with Reference Example 1. As is evident from FIG. 8, although the concentration of coumaramide in the extract gradually increased until a lapse of about 60 minutes after the start of immersion, it became nearly constant thereafter.

Example 8

Cooling Temperature in Crystallization Step

A dry coumaramide crystal was obtained in a similar method to Example 2 except that the temperature when the concentrate by the reverse osmosis membrane was cooled and left at rest for 1 day was varied to be 5° C., 10° C., 20° C., and 25° C. Table 5 lists results of the measurement of the purity and yield of the obtained coumaramide crystals in accordance with the method of Reference Example 2. Table 5 provides a summary of the purity of coumaramide and the yield of coumaramide by the cooling temperature of the crystallization step. As is evident from Table 5, compared to Example 2, in which the temperature at cooling was 15° C., the yield of coumaramide increased at 10° C. and further increased at 5° C. No coumaramide crystal was precipitated at both 20° C. and 25° C.

TABLE 5

| | Cooling temperature | Purity of coumaramide | Yield of coumaramide mg/kg-raw material |
|---|---|---|---|
| Example 8 | 25 | — | 0 |
| | 20 | — | 0 |
| Example 2 | 15 | 92.4% | 920 |
| Example 8 | 10 | 92.6% | 1058 |
| | 5 | 91.2% | 1132 |

Example 9

Temperature at Filtration in Concentration Step

Figure 9:
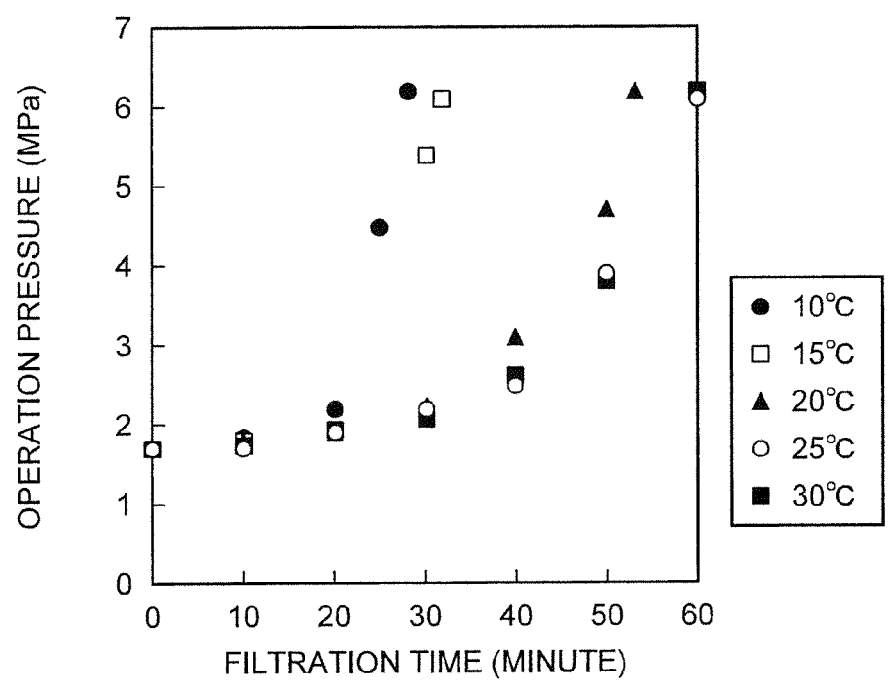
FIG. 9 is a diagram illustrating changes with time of operation pressure when concentrating coumaramide by a reverse osmosis membrane at various temperatures.

The concentration of the coumaramide extract was performed in a similar method to Example 4 except that the temperature at the concentration by the reverse osmosis membrane in the concentration step was varied to be 10° C., 15° C., 20° C., 25° C., and 30° C. FIG. 9 illustrates changes with time of the operation pressure during concentration. Crystal precipitation was visually observed during concentration in any of the conditions of 10° C., 15° C., and 20° C. As is evident from FIG. 9, at filtration temperatures of 10° C. and 15° C., the operation pressure sharply rose compared to the cases of 20° C., 25° C., and 30° C., from which it was inferred that membrane clogging occurred due to the precipitation of the coumaramide crystal.

INDUSTRIAL APPLICABILITY

The obtained coumaramide has high purity and can be used in the production of various chemicals with the coumaramide as a raw material.

The invention claimed is:
1. A method of manufacturing p-coumaramide comprising:

treating cellulose-based biomass with an ammonia-containing treating agent to obtain ammonia-treated biomass;

immersing the ammonia-treated biomass into a solvent containing at least water and eluting p-coumaramide in the ammonia-treated biomass into the solvent to obtain a coumaramide solution;

filtrating the coumaramide solution through a reverse osmosis membrane to concentrate the coumaramide solution on a non-permeate side of the reverse osmosis membrane;

collecting a non-permeate that is the coumaramide solution concentrated on the non-permeate side of the reverse osmosis membrane; and performing crystallization with respect to the non-permeate to precipitate p-coumaramide as a crystal to obtain a p-coumaramide crystal.

2. The method according to claim 1, wherein the p-coumaramide crystal collected at the crystallization has a purity of 90% or higher.

3. The method according to claim 1, wherein the temperature of the solvent used at extraction is 40° C. or higher.

4. The method according to claim 1, wherein the solvent used at extraction contains at least one polar organic solvent.

5. The method according to claim 4, wherein the solvent contains at least ethanol as the polar organic solvent.

6. The method according to claim 1, wherein the liquid temperature of the coumaramide solution filtrated through the reverse osmosis membrane is 20° C. or higher.

7. The method according to claim 1, wherein the crystallization precipitates the p-coumaramide crystal by cooling the coumaramide solution to 15° C. or lower.

8. The method according to claim 1, wherein extraction hydrolyzes the ammonia-treated biomass through addition of a diastatic enzyme when the ammonia-treated biomass is immersed into the solvent.

9. The method according to claim 1, further comprising:
before filtrating the coumaramide solution through the reverse osmosis membrane, purifying by filtrating the coumaramide solution through a nanofiltration membrane and collecting a purified coumaramide solution as a permeate.

* * * * *